(12) United States Patent
Link et al.

(10) Patent No.: US 7,880,029 B2
(45) Date of Patent: Feb. 1, 2011

(54) USE OF POLYALKENYL SUCCINIMIDES IN ACRYLIC ACID PRODUCTION

(75) Inventors: John Link, Humble, TX (US); Sherif Eldin, Bellaire, TX (US)

(73) Assignee: General Electric Company, Schenectady, NY (US)

( * ) Notice: Subject to any disclaimer, the term of this patent is extended or adjusted under 35 U.S.C. 154(b) by 1892 days.

(21) Appl. No.: 10/850,075

(22) Filed: May 19, 2004

(65) Prior Publication Data

US 2005/0261515 A1  Nov. 24, 2005

(51) Int. Cl.
*C07C 69/52* (2006.01)
*C07C 51/16* (2006.01)

(52) U.S. Cl. ........................ 560/205; 562/547
(58) Field of Classification Search ................. 560/205; 562/547
See application file for complete search history.

(56) References Cited

U.S. PATENT DOCUMENTS

| 4,507,495 | A | 3/1985 | Dougherty et al. |
| 4,638,079 | A | 1/1987 | Inskip et al. |
| 4,663,480 | A | 5/1987 | Inskip et al. |
| 4,720,566 | A | 1/1988 | Martin |
| 4,797,504 | A | 1/1989 | Roling |
| 5,171,888 | A | 12/1992 | Roling |
| 5,705,721 | A | 1/1998 | Patel |
| 5,789,356 | A | 8/1998 | Tiffany, III |
| 6,281,386 | B1 | 8/2001 | Fauconet et al. |
| 6,770,219 | B2 | 8/2004 | Tong |
| 2003/0150153 | A1 | 8/2003 | Henry, Jr. et al. |

FOREIGN PATENT DOCUMENTS

EP  0 532 264 A2  3/1993

OTHER PUBLICATIONS

International Search Report for PCT/US2005/014227, Aug. 18, 2005, 3 pgs.

*Primary Examiner*—James O Wilson
*Assistant Examiner*—Ebenezer Sackey
(74) *Attorney, Agent, or Firm*—Duane Morris LLP

(57) ABSTRACT

A method for dispersing polymerization by-products and maintaining said by-products in suspension in a hydrocarbon processing system during acrylic acid and acrylate monomer formation is disclosed, which includes adding to the monomer an effective inhibiting amount of an N-alkyl polyalkenyl succinimide dispersant.

7 Claims, No Drawings

USE OF POLYALKENYL SUCCINIMIDES IN ACRYLIC ACID PRODUCTION

FIELD OF THE INVENTION

The present invention pertains to methods and compositions for dispersing polymerization by-products and maintaining said by-products in suspension in a hydrocarbon processing system, during processes such as acrylic acid monomer preparation and purification.

BACKGROUND OF THE INVENTION

Polymerizable acrylic acid and other acrylate monomers undesirably polymerize during various stages of the manufacturing, processing, handling, storage and use thereof. One especially troublesome problem is the polymerization of acrylic acid monomer in the purification stages of monomer production. It is well known that the monomers readily polymerize and that such polymerization increases with concurrent increases in temperature.

Common industrial methods for producing acrylic acids include a variety of purification processes, including distillation, to remove impurities. Unfortunately, purification operations carried out at elevated temperatures result in an increased rate of undesired polymerization. Polymerization during the monomer purification process results not only in the loss of desired monomer end-product, but also in the loss of production efficiency caused by polymer formation or agglomeration on process equipment. In heat requiring operations, such agglomeration adversely affects heat transfer and separation efficiency.

A variety of compositions and methods have been proposed for inhibiting uncontrolled polymerization of acrylic acid and esters. Known inhibitors include phenothiazine, methylene blue, hydroquinone, hydroquinone methyl ether (MEHQ), copper compounds, 4-hydroxy-TEMPO and sundry manganese containing compounds.

In U.S. Pat. No. 4,797,504, hydroxylamines and phenylenediamines, in combination, are taught as being effective anti-polymerization aids for acrylate monomer systems. This particular combination has also been shown to be effective in inhibiting acrylonitrile polymerization in U.S. Pat. No. 4,720,566.

Japanese patent publication 50098211 teaches that polymerization of α, β unsaturated carboxylic acids can be inhibited by the use of sundry manganese salts, with or without hydroquinone or MEHQ, save for the particular sodium manganese ethylene diamine tetra-acetate salt. Similarly in U.S. Pat. No. 4,507,495, acrylic acid polymerization is inhibited in ethyl acrylate production methods by the use of manganese or cerium salts that are soluble in the reaction mixture. Manganese nitrite, $Mn(NO_2)_2$, is used as a polymerization inhibitor in U.S. Pat. No. 4,663,480.

Of somewhat lesser importance is U.S. Pat. No. 4,638,079 which discloses processes for inhibiting polymerization of polymerizable ethylenically unsaturated monomers such as hydrocarbons, acids and esters wherein a cobalt (III), nickel (II), or manganese (II) complex of N-nitrosophenylhydroxylamine is utilized. In a preferred embodiment of that patent, polymerization of an acrylic acid or acrylate ester is inhibited.

It is desirable to provide a low volatility anti-polymerization treatment so that the treatment will not be carried overhead with the purified monomer during the distillation (i.e., purification) thereof. Some plants will take crude acrylic acid from the bottom of a tower and transfer it to a storage tank, prior to further purification to technical grade, glacial or to esterification.

There has been a specific need for an acrylate anti-polymerization treatment that is readily soluble in non-polar organic solvents, such as xylene or heavy aromatic naphtha, so that the treatment can be dissolved therein and provide a stable product that can be shipped and stored without undue fear of product deterioration and separation. Related treatments are found in, e.g., U.S. Pat. No. 5,171,888.

As noted above, the commercial purification of acrylic acid entails multiple separation steps that result in the formation of unwanted polyacrylic acid in such quantities that the distillation process must be terminated and the distillation tower cleaned of the unwanted polymer. Polymerization inhibitors are continuously injected, but polymer still builds up on distillation trays and in column reboilers.

Polyalkenyl succinimide dispersants, e.g., various polyisobutenyl succinimide (PIBSI) dispersants of relatively high molecular polyisobutenyl weight have been used to disperse polymer into extraction solvents, and are able to mitigate fouling where there are high concentrations of solvent, and low concentrations of acrylic acid. These same PIBSI dispersants have not been successful in locations where there is little to no solvent and high concentrations of acrylic acid, because these dispersants are not soluble in the acrylic acid monomer. It would be desirable to find a succinimide dispersant that would be soluble in acrylic acid and acrylate esters.

These and other needs in the art are addressed by the methods and compositions detailed herein.

SUMMARY OF THE INVENTION

The present invention relates to a method for dispersing polymerization by-products and maintaining said by-products in suspension in a hydrocarbon processing system during acrylic acid and acrylate monomer formation, comprising adding to the monomer an effective amount of an N-alkyl (substituted or non-substituted) polyalkenyl succinimide with a polyalkylene number average molecular weight of from about 150-900.

DETAILED DESCRIPTION OF THE INVENTION

In accordance with the present invention, a polyalkenyl succinimide compound is used to disperse polymerization by-products in a hydrocarbon processing system during acrylic acid and other acrylate monomer formation. The compound serves to prevent such by-products from aggregating and depositing in process equipment. The phrase "polymerization by-products" as used herein is intended to include e.g., unwanted polyacrylic acid and other insoluble polymers and by-products. The phrase "acrylic acid monomers" as used herein is intended to include e.g., acrylic acid, methacrylic acid, crotonic acid, isocrotonic acid, acrylate esters, methyl methacrylate and methacrylic esters. This treatment results in polymer being kept from adhering to distillation tower trays and heat exchange surfaces during acrylic acid purification, thereby extending the time the towers can run before having to be shut down for cleaning, as well as minimizing cleaning time.

In a preferred embodiment, the present invention relates to a method for dispersing polymerization by-products and maintaining said by-products in suspension in a hydrocarbon processing system during acrylic acid and acrylate monomer formation, comprising adding to the monomer an effective amount of a polyisobutenyl or polybutenyl succinimide with a polyisobutylene or polybutylene number average molecular weight of from about 150-900. A polyisobutenyl or polybutenyl succinimide with a polyisobutylene or polybutylene number average molecular weight of about 300-600 is more preferred, with a number average molecular weight of about 450 being most preferred.

In a further preferred embodiment, from about 0.001-90% by weight of the polyalkenyl succinimide is added to the acrylate monomer-containing stream. The total amount of treatment is preferably from about 1 ppm to about 1000 ppm based on the weight of the acrylic acid monomer. Most preferably, the total amount of the aforesaid compounds is from 5 ppm to about 500 ppm based on the weight of the monomer.

In the testing of the present invention, laboratory results demonstrated that 1-90% by weight of a polyalkenyl succinimide with a polyisobutylene (PIB) number average molecular weight of about 450 in acrylic acid and butyl acrylate were completely miscible, while polyalkenyl succinimides with a PIB number average molecular weight of 950-1300 in acrylic acid and butyl acrylate were not miscible in the same range. Thus, by reducing the molecular weight of the polyalkene (polyisobutene)lipophile, a PIBSI that was soluble in acrylic acid and acrylate esters was found to be effective for purposes of the present invention.

Results are shown in Table I, below. Sample A was tested in a commercial acrylic acid production unit. Injection rates were varied to achieve concentrations of the active PIBSI between 50 to 175 ppm in the process stream. There was no notable improvement in tower performance over the untreated base case. Sample G was injected into a commercial acrylic acid production unit at a rate of 100 ppm and notable improvement was observed. As an example of the improvement, distillation tower bottoms pump strainer cleanings, which foul with polymer, were reduced by more than 80% over the same time period as the untreated base case.

While the present invention has been described with respect to particular embodiments thereof, it is apparent that numerous other forms and modifications of the invention will be obvious to those skilled in the art. The appended claims and the present invention generally should be construed to cover all such obvious forms and modifications which are within the true spirit and scope of the present invention.

What is claimed is:

1. A method for dispersing polymerization by-products and maintaining said by-products in suspension in a hydrocarbon processing system during acrylic acid and acrylate monomer formation, comprising adding to the monomer an effective amount of an N-alkyl polyalkenyl succinimide with a polyalkylene number average molecular weight of from about 150-900.

2. The method as recited in claim 1, wherein said polyalkenyl succinimide is a polyisobutenyl or polybutenyl succinimide.

3. The method as recited in claim 1, wherein from about 0.001-90% by weight of said polyalkenyl succinimide is miscible in the monomer.

4. The method as recited in claim 1, wherein the amount of polyalkenyl succinimide added to the monomer is from about 1 ppm to about 1000 ppm based on the weight of the monomer.

5. The method as recited in claim 4, wherein the amount of polyalkenyl succinimide added to the monomer is from about 5 ppm to about 500 ppm based on the weight of the monomer.

6. The method as recited in claim 1, wherein said hydrocarbon processing system comprises a distillation tower.

TABLE I

| Commercially Available PIBSI Samples | | | Acrylic Acid Solubility (Wt. Percent) | | | | | Butyl Acrylate Solubility (Wt. Percent) | | | | |
| --- | --- | --- | --- | --- | --- | --- | --- | --- | --- | --- | --- | --- |
| Sample | Alkenyl Group | Solvent | 0.05% | 0.25% | 0.50% | 1.00% | Foam | 0.05% | 0.25% | 0.50% | 1.00% | Foam |
| A | 1300 MW PIB | 30% Mineral Oil | Turbid @ Amb. T T = 50° C. still turbid | Turbid @ Amb. T T = 50° C. still turbid | Turbid @ Amb. T T = 50° C. still turbid | Turbid @ Amb. T T = 50° C. still turbid | No | Solids | Solids | Solids | Solids | No |
| B | 950 MW PIB | 27% Mineral Oil | Translucent | Turbid @ Amb. T | Turbid @ Amb. T | Turbid @ Amb. T | No | NA | Solids | Solids | Solids | No |
| C | 1000 MW PIB | 55% Mineral Oil | Translucent | Turbid @ Amb. T | Turbid @ Amb. T | Turbid @ Amb. T | No | NA | Solids | Solids | Solids | No |
| D | 1000 MW PIB | 55% Mineral Oil | Translucent | Turbid @ Amb. T | Turbid @ Amb. T | Turbid @ Amb. T | No | NA | Solids | Solids | Solids | No |
| E | 950 MW PIB (Borated) | 43% Mineral Oil | Translucent | Turbid @ Amb. T | Turbid @ Amb. T | Turbid @ Amb. T | No | NA | Solids | Solids | Solids | No |
| F | 950 MW PIB | 45% Mineral Oil | Translucent | Turbid @ Amb. T | Turbid @ Amb. T | Turbid @ Amb. T | No | NA | Solids | Solids | Solids | No |
| G | 450 MW PIBSI | 25% Mineral Oil | Soluble | Soluble | Soluble | Soluble | No | NA | Soluble | Soluble | Soluble | No |
| Mineral Oil | N/A | 100% Mineral Oil | Soluble | Soluble | Soluble | Soluble | No | NA | NA | NA | NA | NA |

Note:
PIB = polyisobutenyl; Amb. = Ambient; T = temperature

7. The method as recited in claim 1, wherein the N-alkyl of said N-alkyl polyalkenyl succinimide is substituted or non-substituted.

* * * * *